United States Patent

Swartz et al.

[11] Patent Number: 5,810,730
[45] Date of Patent: Sep. 22, 1998

[54] GUIDING INTRODUCER FOR RIGHT ATRIUM

[76] Inventors: John Frederick Swartz, 2935 E 75th, Tulsa, Okla. 74136; John D. Ockuly; John J. Fleischhacker, both of 14901 DeVeau Pl., Minnetonka, Minn. 55356-9595; James A. Hassett, 11327 Louisiana Cir., Bloomington, Minn. 55438

[21] Appl. No.: 392,057

[22] Filed: Feb. 22, 1995

Related U.S. Application Data

[62] Division of Ser. No. 146,744, Nov. 3, 1993, Pat. No. 5,427,119.

[51] Int. Cl.[6] .......................................................... A61B 6/00
[52] U.S. Cl. ........................... 600/434; 604/280; 604/281
[58] Field of Search ..................................... 604/281, 280, 604/282; 128/642, 786; 607/122

[56] References Cited

U.S. PATENT DOCUMENTS

| 4,641,649 | 2/1987 | Walinsky et al. | 128/303.1 |
| 4,785,815 | 11/1988 | Cohen | 128/642 |
| 5,120,323 | 6/1992 | Shockey et al. | 604/282 |

*Primary Examiner*—Max Hindenburg
*Assistant Examiner*—Pamela Wingood

[57] ABSTRACT

A guiding introducer for use in the right atrium comprised of a first, second and third section wherein the first section is a generally elongated straight section wherein merged with the distal end of the first section is a second section which is curved upward in a longitudinal curve wherein the distal end of the second section is merged with the third section. The guiding introducer is for use in sensing, pacing and ablating procedures in the right atrium of the human heart.

17 Claims, 6 Drawing Sheets

1) TRICUSPID VALVE
2) FOSSA OVALIS (PATENT)
3) LIMBUS OF FOSSA OVALIS
4) SHEATH
5) CATHETER

GUIDING INTRODUCER FOR RIGHT ATRIUM

This is a divisional application of Ser. No. 08/146,744, filed on Nov. 3, 1993, U.S. Pat. No. 5,427,119.

BACKGROUND OF INVENTION

1. Field of Invention

This invention relates to introducers. More particularly, this invention relates to guiding introducers of specific shapes for use within the right atrium of the human heart.

2. Prior Art

Introducers and catheters have been in use for medical procedures for many years. For example, one use has been to convey an electrical stimulus to a selected location within the human body. Another common use is to monitor and make measurements for diagnostic tests within the human body. Thus, catheters may examine, diagnose and treat while positioned at a specific location within the body which are otherwise inaccessible without more invasive procedures. In use, catheters may be inserted into a major vein or artery which is near the body surface. The catheters are then guided to the specific location for examination, diagnosis or treatment by manipulating the catheter through the artery or vein of the human body.

Catheters have become increasingly useful in remote and difficult to reach locations within the body. However, the utilization of these catheters is frequently limited because of the need for the precise placement of the tip of the catheter at a specific location within the body.

Control of the movement of catheters to achieve such precise placement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery, vein or body part while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the tip of the catheter reaches the desired location in the heart.

The distal end of a catheter used in such a procedure is sometimes preformed into a desired curvature so that by torquing the catheter about its longitudinal axis, the catheter can be manipulated to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 4,117,836 discloses a catheter for the selective coronary angiography of the left coronary artery and U.S. Pat. Nos. 5,016,640 and 4,883,058 disclose catheters for use in selective coronary angiography of the right coronary artery. See also U.S. Pat. No. 4,033,031. Finally, U.S. Pat. No. 4,898,591 discusses a catheter with inner and outer layers containing braided portions. The '591 patent also discloses a number of different curvatures for intravascular catheters.

Thus, there are a number of patents which disclose catheters with predetermined shapes, designed for use in specific medical procedures generally associated with the heart or the vascular system. Because of precise physiology of the heart and the vascular system, catheters or introducers with carefully designed shapes for predetermined uses within the human heart and vascular system are important.

Accordingly, it is an abject of this invention to prepare a guiding introducer for selected medical procedures in the right atrium.

It is a further object of this invention to prepare a guiding introducer for use in selected electrophysiology procedures within the right atrium of the heart.

Another object of this invention is to prepare a guiding introducer for use in selected ablation procedures within the right atrium of the heart.

These and other objects are obtained by the design of the guiding introducers disclosed in the instant invention.

SUMMARY OF INVENTION

The instant invention is a guiding introducer to be used in the right atrium comprised of a first, second and third sections wherein the first section is a generally elongated straight section which is merged at its distal end with the second and third sections which form a complex curve.

DETAILED DESCRIPTION OF THE DRAWINGS

Figure 1:
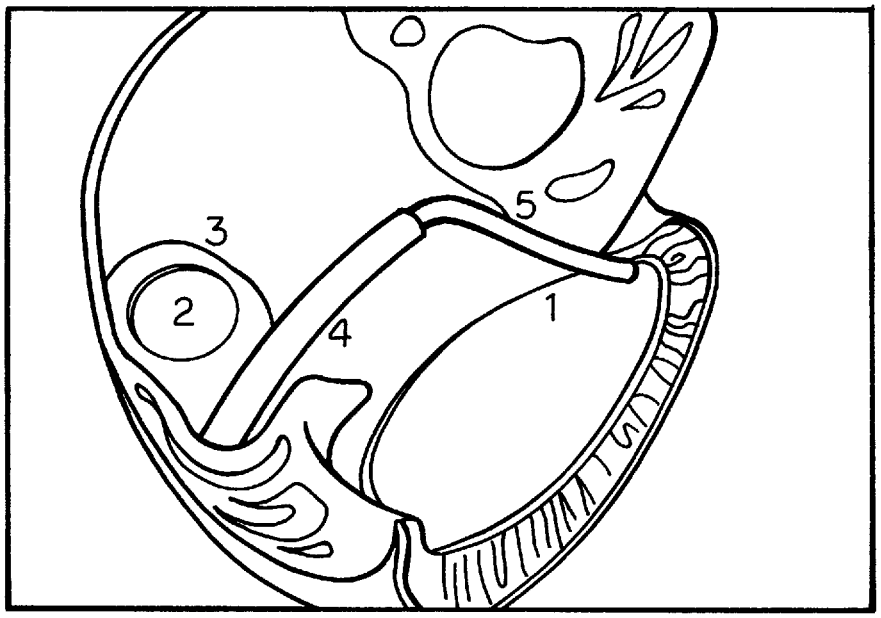
FIG. 1 is a cross-section of the right side of the heart showing the right atrium and ventricle and the placement of the guiding introducer.

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve (1) contained within the atrioventricular septum communicates the right atrium with the right ventricle. On the inner wall of the right atrium where it is connected with the left atrium is a recessed portion, the fossa ovalis (2). See FIG. 1. In the heart of a fetus, the fossa ovalis is open, permitting the fetal blood to flow between the right and left atria. In most individuals, this opening closes after birth, but in as many as 25 percent of individuals an opening still remains in the fossa ovalis between the right and left atria. Between the fossa ovalis and the tricuspid valve is the opening or ostium for the coronary sinus. The coronary sinus is the large epicardial vein which accommodates most of the venous blood which drains from the myocardium into the right atrium.

In the normal heart, contraction and relaxation of the heart muscle (myocardium) takes place in an organized fashion as electro-chemical signals pass sequentially through the myocardium from the atrial to the ventricular tissue along a well defined route which includes the His-Purkinje system. Initial electrical impulses are generated at the sinuatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, a common arrhythmia is Wolff-Parkinson-White syndrome (W-P-W). The cause of W-P-W is the existence of an anomalous conduction pathway or pathways that connects the atrial muscle tissue directly to the ventricular muscle tissue, thus by-passing the normal His-Purkinje system. These pathways are usually located in the fibrous tissue that connects the atrium and the ventricle. In recent years a technique has been developed to destroy these anomalous conduction pathways by delivering energy into the tissue in which the pathways exist. To accomplish this procedure a special electrode catheter is positioned as close as possible to the anomalous conduction pathway to maintain constant tissue contact while energy is delivered to destroy the pathway. This same type of contact with the cardiac tissue is also necessary when mapping or other procedures are employed relating to these pathways.

One end of these anomalous conduction pathways can be located either in the right atrium or in the left atrium with the other end of the pathway located in the ventricle. When the anomalous conduction pathway is located between the left atrium and the left ventricle, there are two approaches to positioning the catheter near the pathway for the appropriate medical procedure. One is to introduce the catheter into the femoral artery by a standard introducer sheath and advance it up the aorta, across the aortic valve into the left ventricle and then attempt to position its tip under the mitral valve annulus near the anomalous conduction pathway. This approach is frequently difficult for many reasons, including the structure of the left ventricle, the fact that it requires arterial access and potential problems associated with ablation of ventricular tissue such as sudden cardiac death. The other approach is to introduce a transseptal sheath apparatus, a long single plane curve introducer, into the right femoral vein and advance it through the inferior vena cava into the right atrium. A puncture is then made through the fossa ovalis in the interatrial septum and the apparatus is advanced into the left atrium where the trocar and dilator of the apparatus are removed, leaving the sheath in position in the left atrium. The mapping or ablation catheter is then inserted through the sheath and into the left atrium and positioned on top of the mitral valve annulus near the anomalous conduction pathway. Specific positions may be chosen for the mapping or ablation on the left side of the heart, including specifically posterorseptal, posterior, posterorlateral, lateral and antero lateral positions around the mitral valve annulus.

Traditionally, there have been two techniques for locating and ablating anomalous conduction pathways which are situated between the right atrium and right ventricle. Either method can be initiated by advancing a catheter through an access site into a vein in the leg, neck or upper chest.

The first technique, which approaches the pathway from the pathway's ventricular insertion site, involves entering the right atrium from either the inferior or superior vena cava, passing through the tricuspid valve, and advancing toward the apex of the right ventricle. Then the catheter is directed to make a 180 degree turn to reverse its path back up toward the right atrium and locate the accessory pathway under the tricuspid valve apparatus. The accessory paythway is then ablated from the ventricular insertion site under the tricuspid valve.

The second technique, which approaches the pathway from the atrial insertion site, is to enter the right atrium from the inferior or superior vena cava, and attempt to locate the atrial insertion site of the accessory pathway around the tricuspid valve (1) annulus. The accessory pathway is then ablated from the pathway's atrial insertion site on the atrial aspect of the tricuspid valve.

AV nodal pathways can be located and ablated from the right atrium.

Mere introduction of the catheter into the right atrium is not sufficient to effectively and efficiently perform these medical procedures, especially the mapping or ablation of the anomalous conduction pathways. These medical procedures are usually performed using a specific catheter. The medical practitioners monitor the introduction of the catheter and its progress through the vascular system by a fluoroscope. However, such fluoroscopes do not easily identify the specific features of the heart in general and the critically important structures of the right atrium in specific, thus making placement of the catheter difficult. This placement is especially difficult as the beating heart is in motion and the catheter will be moving within the right atrium as blood is being pumped through the heart throughout the procedure. The structure and shape of the guiding introducer of the instant invention addresses and solves these problems.

Figure 2:
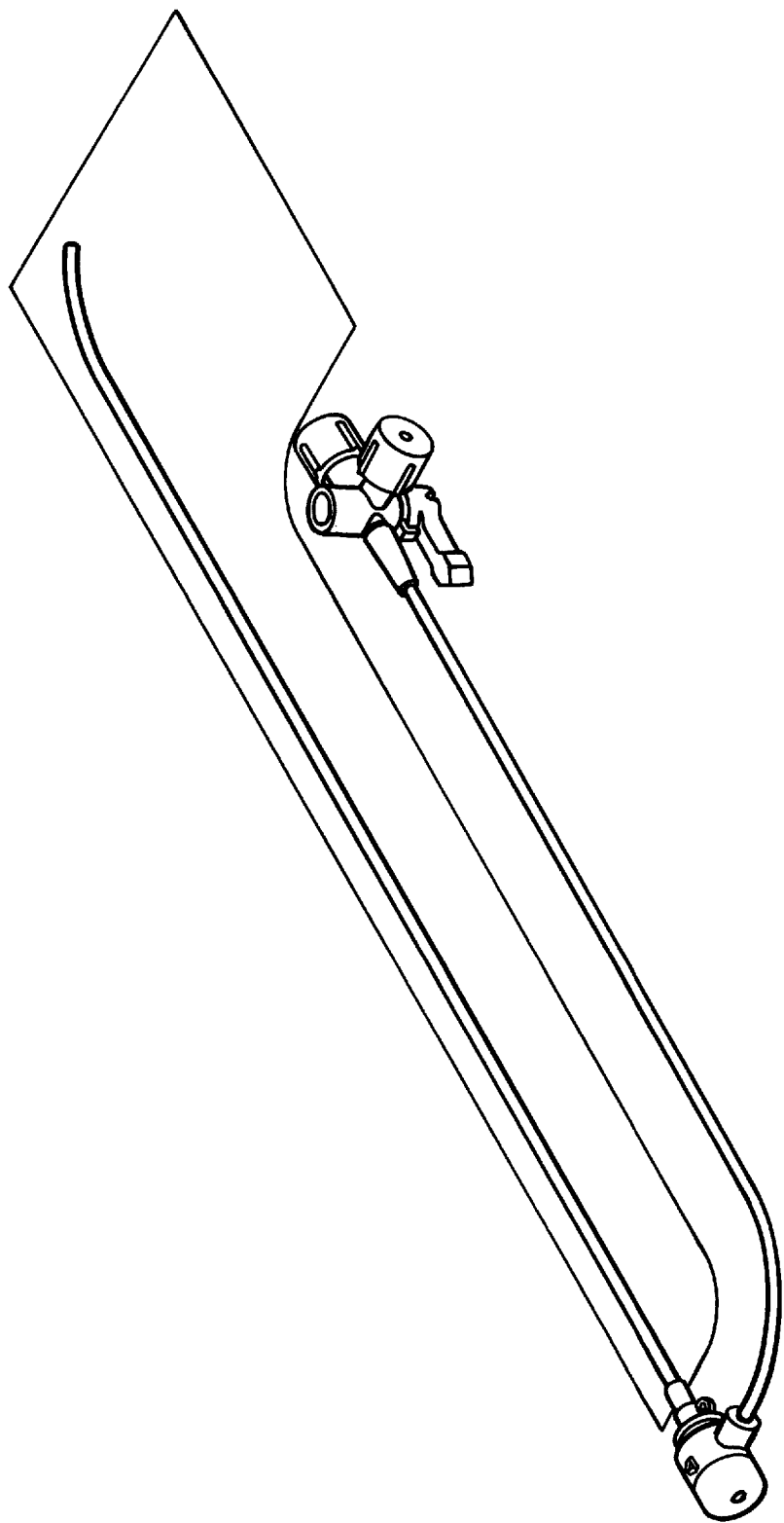
FIG. 2 is a perspective view of the first embodiment of the guiding introducer.

Referring now to FIG. 2, the guiding introducer or sheath (4) of the present invention for use in the right atrium is comprised of a first, second and third section. The first section is a conventional, generally elongated, hollow straight section of sufficient length for introduction into the patient and for manipulation from the point of insertion to the specific desired location within the heart.

Merged with the distal end of the first section of the introducer is the second section which is a curved section, curved in a longitudinal curve with a radius of from about 0.5 cm. to about 2.0 cm., preferably about 1.5 cm. to form an arc of approximately 40 to about 60 degrees, preferably about 45 to about 55 degrees and most preferably about 50 degrees. Preferably, this section is from about 0.2 cm. to about 2.0 cm. in overall length, most preferably 0.5 cm. to about 1.0 cm.

The third section of the introducer is merged with the distal end of the second section. The shape of the third section of the guiding catheter will depend on the location within the right atrium which is being treated. In one embodiment the guiding introducer is used to place a mapping or ablating catheter in a position close to AV nodal pathways or posterorseptal and septal accessory pathways. See FIG. 2. To accomplish this placement, the third section is comprised of a generally straight section directed upward at an angle of about 40 to about 60 degrees from the plane of the first section, preferably 45 to about 55 degrees and, most preferably, about 50 degrees, wherein said third section is approximately 0.5 cm. to about 3.0 cm. in length, preferably from about 0.5 cm. to about 2.0 cm. in length and, most preferably, about 0.5 cm. to about 1.5 cm. in length. See FIG. 2. This generally straight section provides torque control while the guiding introducer is being manipulated through the inferior vena cava.

Figure 3:
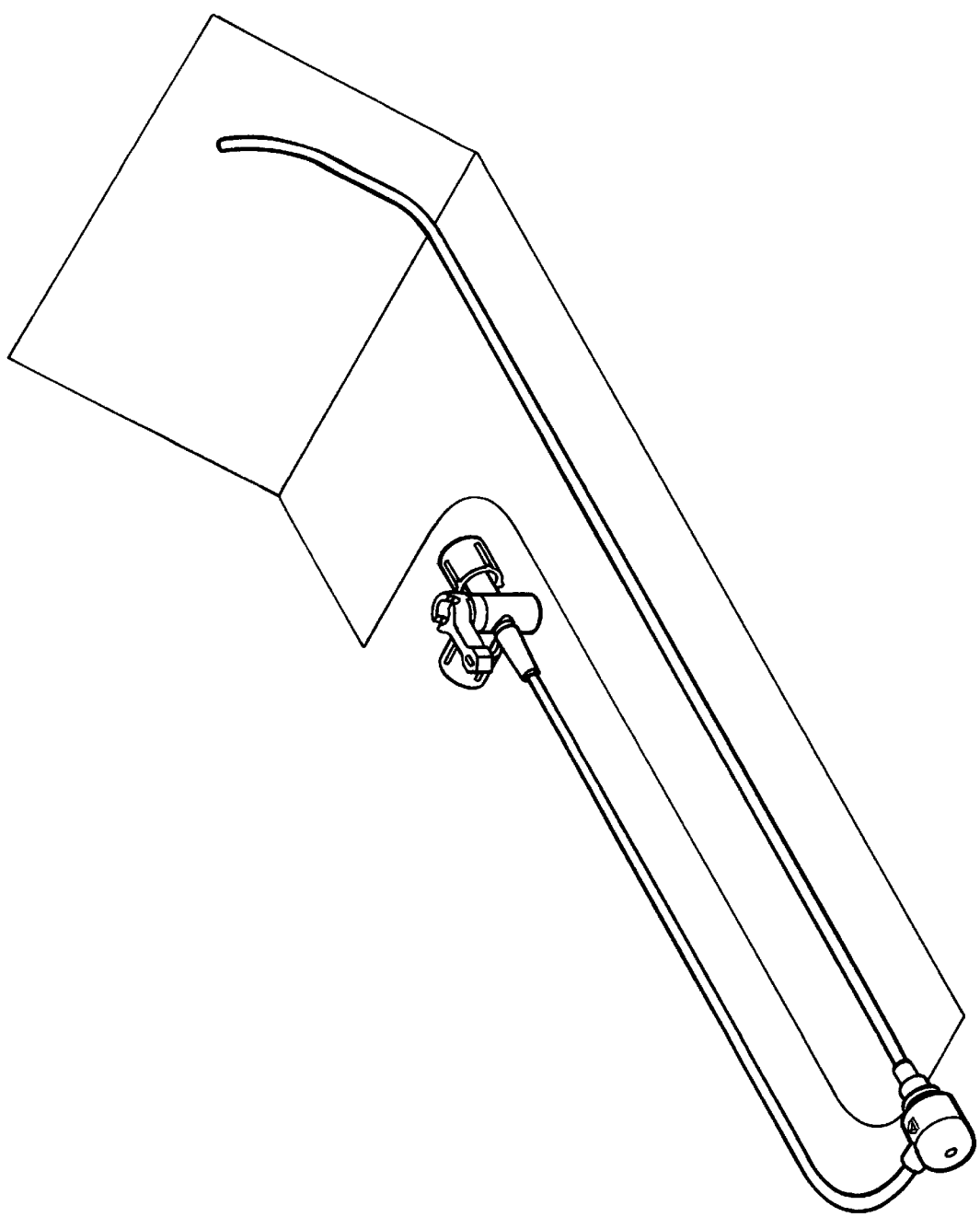
FIG. 3 is a perspective view of a second embodiment of the guiding introducer.

To place the sensing or ablation catheters at a location for analysis and treatment of anteroseptal to anterior accessory pathways, the third section of the guiding introducer is elongated by merging onto the generally straight section of the third section a longitudinally curved section curved to the left, wherein this longitudinal curve has a radius of about 1.0 to about 4.0 cm., preferably from about 1.5 to about 3.0 cm. and most preferably about 2.0 to about 3.0 cm. See FIG. 3. Further, this longitudinal curve of said third section is substantially (within about 15 degrees) coplanar with the generally straight section of the third section. When used for analysis and treatment of the anteroseptal to anterior accessory pathways, the arc of this longitudinally curved section of the third section has an arc of about 35 to about 55 degrees, preferably from about 40 to about 50 degrees and, most preferably, about 45 degrees.

Figure 4:
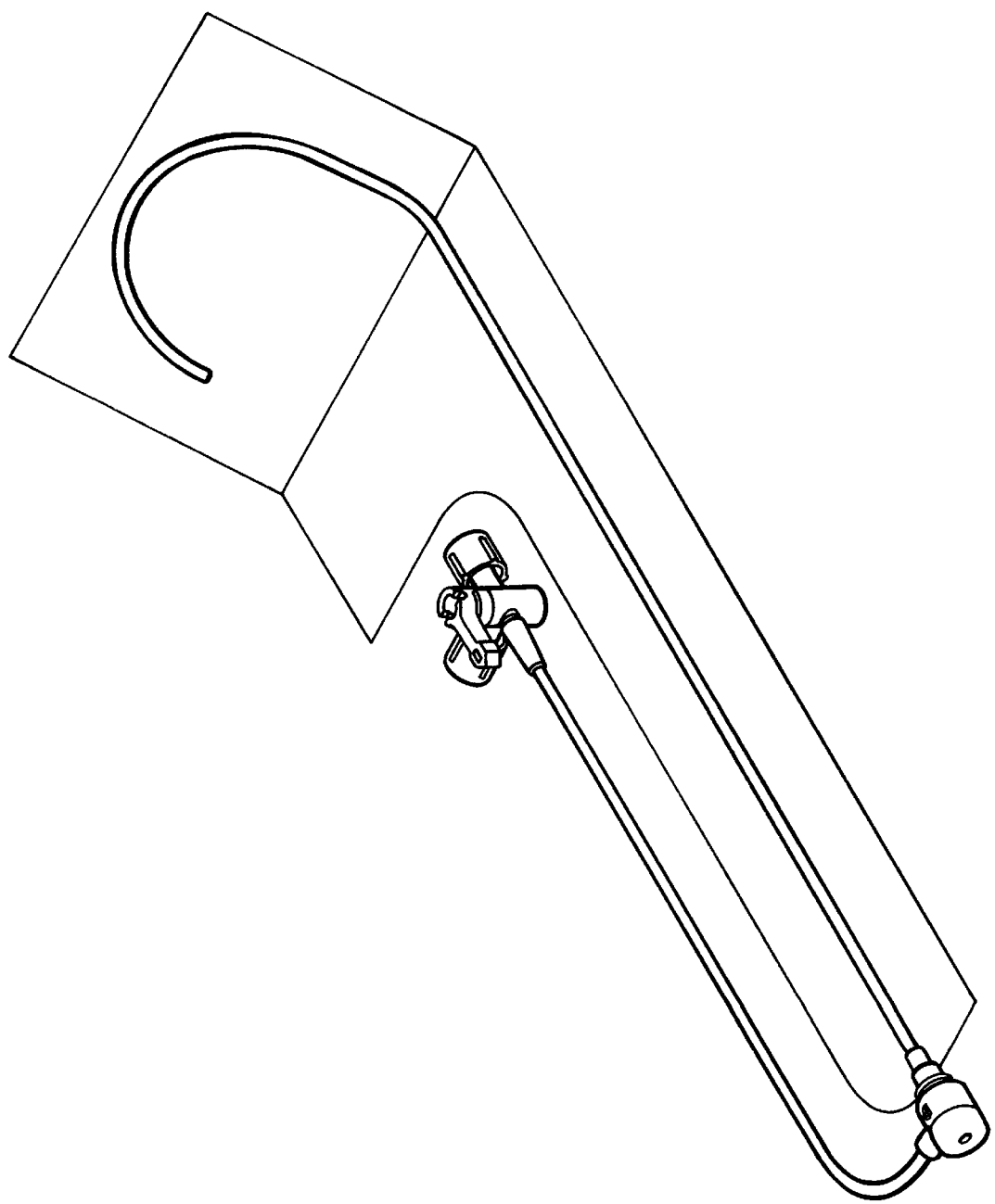
FIG. 4 is a perspective view of a third embodiment of the guiding introducer.

This guiding introducer can also be used for analysis and treatment of anterior to anterolateral accessory pathways adjacent to the tricuspid valve annulus. For this use the longitudinally curved section of the third section is comprised of an arc with the radius of about 80 to about 100 degrees, preferably from about 85 to about 95 degrees and, most preferably, about 90 degrees. See FIG. 4.

Figure 5:
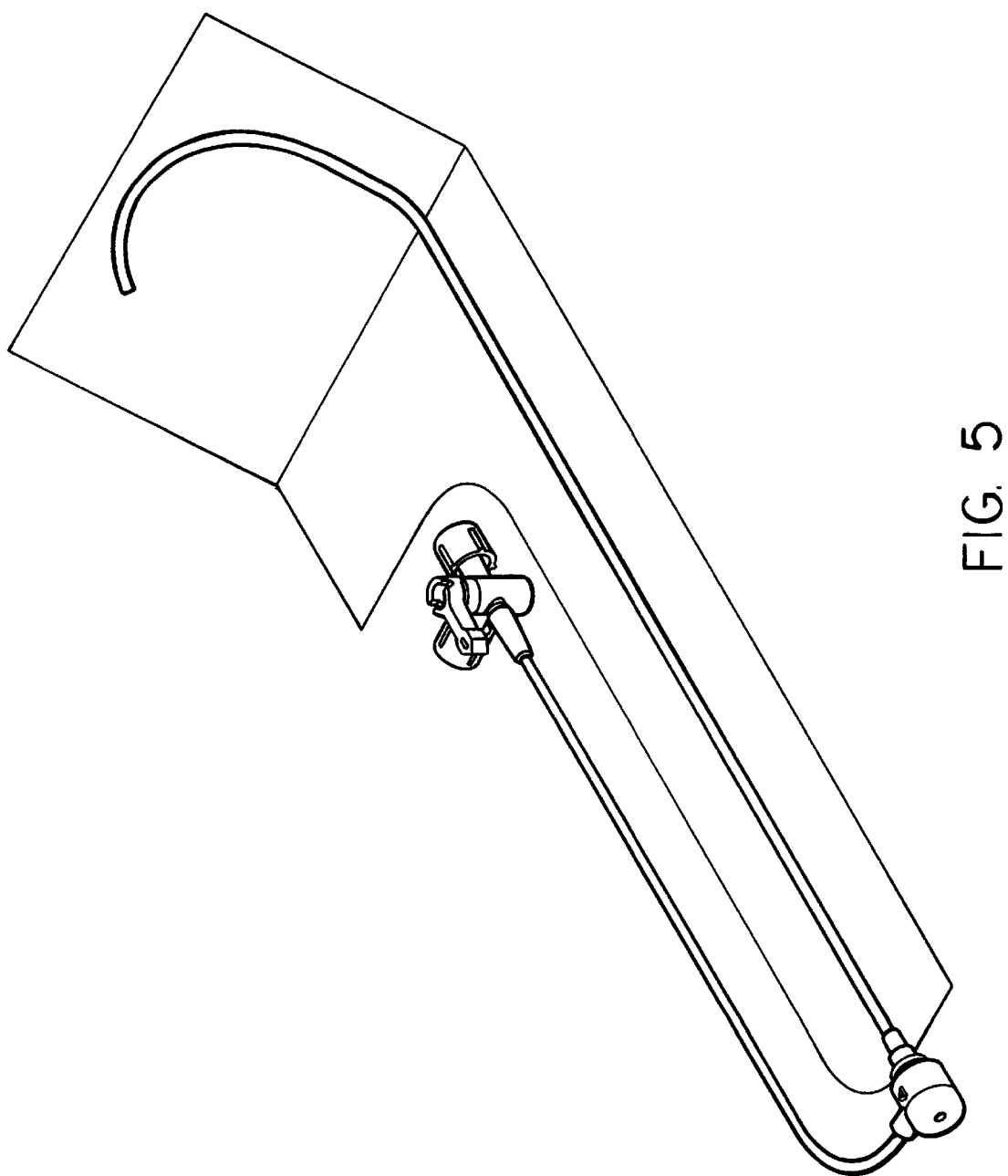
FIG. 5 is a perspective view of a fourth embodiment of the guiding introducer.

The guiding introducer may also be used for analysis and treatment of anterolateral to lateral accessory pathways, on the atrial aspect of the tricuspid valve annulus. In this embodiment the longitudinally curved section is comprised of an arc with a radius of about 125 to about 145 degrees, preferably 130 to about 140 degrees and, most preferably about 135 degrees. See FIG. 5.

Figure 6:
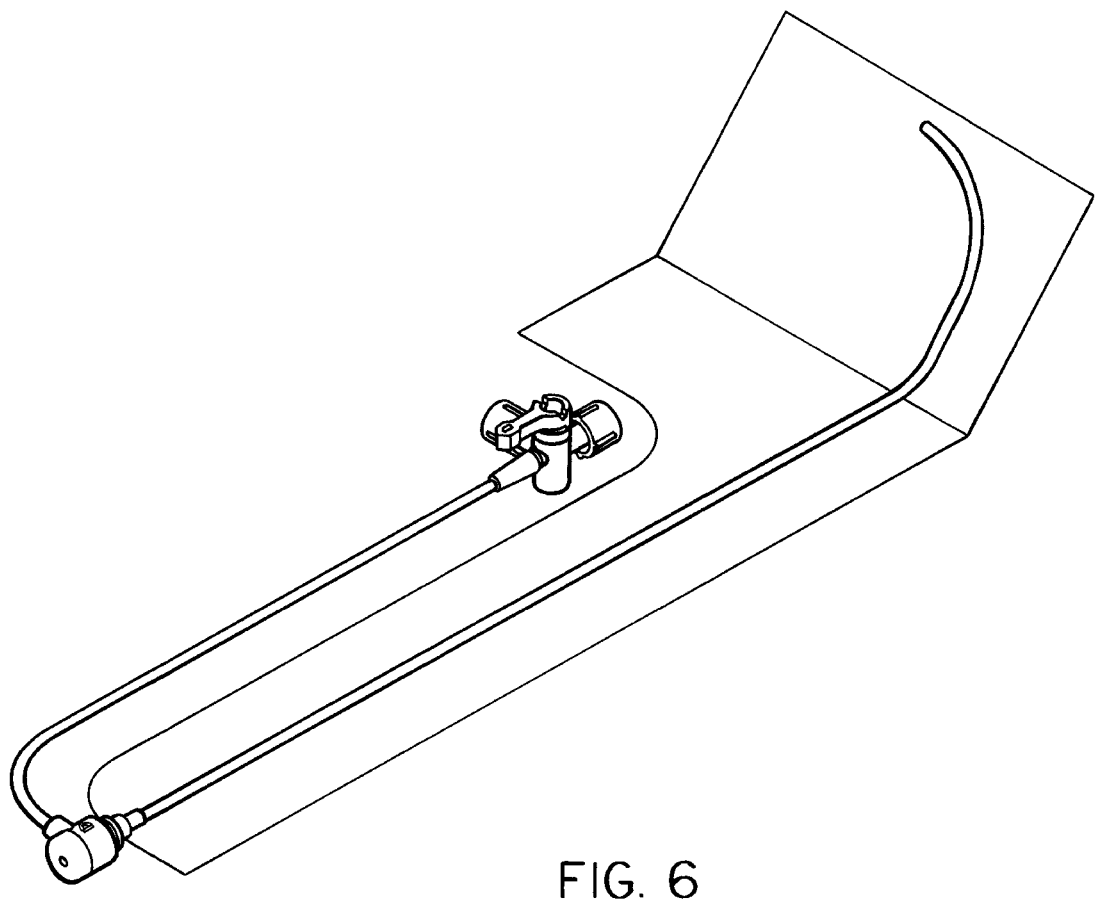
FIG. 6 is a perspective view of a fifth embodiment of the guiding introducer.

The guiding introducer may also be used for analysis and treatment of lateral to posterorlateral accessory pathways adjacent to the tricuspid valve by the longitudinally curved section of the third section comprising an arc with a radius of about 170 to about 190 degrees, preferably 175 to about 185 degrees and, most preferably about 180 degrees. See FIG. 6.

The distal tip of the introducer may be, and generally will be, tapered to form a good transition with the dilator as is the case with many introducers.

The guiding introducer may be made of any material suitable for use in humans, which has a memory or permits distortion from and subsequent substantial return to the desired three dimensional or complex multi-planar shape. For the purpose of illustration and not limitation, the internal diameter of the tip of the guiding introducer may vary from about 6 to about 10 "French" (1 French equals about ⅓ of a millimeter). Such introducers can accept dilators from about 6 to about 10 French and appropriate guidewires. Obviously if larger, or smaller dilators and catheters are used in conjunction with the guiding introducer of the instant invention, modification can be made in the size of the instant guiding introducers.

The guiding introducer preferably contains one or a multitude of radioopaque tip marker bands near the terminus of the guiding introducer. While various modifications may be made in the shapes by increasing or decreasing its size or adding additional tip markers, it is critical to the successful placement of the guiding introducer within the right atrium that the preferred shape be maintained.

The guiding introducer also preferably contains one or a plurality of vents near the distal tip of the introducer, preferably 3 or 4 or such vents. The vents are preferably located no more than about 5 to 6 cm. from the tip of the introducer and more preferably 0.5 cm. to about 4.0 cm. from the tip. The size of these vents should be in the range of about 20 to 60 1/1000 of an inch in diameter. These vents are generally designed to prevent air embolisms from entering the introducer caused by the withdrawal of a catheter contained within the guiding introducer in the event the distal tip of the introducer is occluded. For example, if the tip of the introducer is placed against the myocardium and the catheter located within the introducer is withdrawn, a vacuum may be created within the catheter if no vents are provided. If such vacuum is formed, air may be forced back into the introducer by the reintroduction of a catheter into the lumen of the introducer. Such air embolism could cause significant problems on the patient including the possibility of a stroke, heart attack or other such problems common with air embolism in the heart. The addition of vents near the distal tip of the guiding introducers prevents the formation of such vacuum by permitting fluid, presumably blood, to be drawn into the lumen of the introducer as the catheter is being removed, thus preventing the possibility of formation of an air embolism.

Variances in size or shape of the instant guiding introducer are also intended to encompass pediatric uses for the guiding introducer of the instant invention, although the preferred use is for adult human hearts. It is well recognized that pediatric uses may require reductions in size of the various sections of the introducer in particular the first section, but without any significant modification to the shape or curves of the guiding introducer.

In operation, a modified Seldinger technique is normally used for the insertion of the catheter into either an artery or vein of the body. Using this procedure, a small skin incision is made at the appropriate location to facilitate the catheter and dilator passage. The subcutaneous tissue is then dissected, followed by a puncture of the vessel with an appropriate needle with stylet positioned at a relatively shallow angle. The needle is then partially withdrawn and reinserted at a slightly different angle into the vessel, making sure that the needle remains within the vessel. A soft flexible tip of an appropriate sized guidewire is then inserted through and a short distance beyond the needle into the vessel. Firmly holding the guidewire in place, the needle is removed. The wire guide is then advanced through the vessel into the inferior vena cava or the right atrium. With the wire guide in place, either in the inferior vena cava or into the right atrium, a dilator is then placed over the wire with the guiding introducer or sheath (4) placed over the dilator. The dilator and guiding introducer generally form an assembly to be advanced together along the guidewire into the inferior vena cava or into the right atrium. The guidewire is then withdrawn as is the dilator, leaving the guiding introducer either in the inferior vena cava or in the right atrium. If the guiding introducer has been left in the inferior vena cava, it is then advanced up the inferior vena cava into the right atrium. If analysis or treatment of the AV nodal pathways or posterorseptal or septal accessory pathways is necessary, the truncated third section of the instant guiding introducer is used. See FIG. 2. When the longitudinal curve is added at the distal end of the third section, the guiding introducer tends to conform to the inside surface of the anterior right atrium just superior to the tricuspid annulus for use on the various accessory pathways located near the tricuspid valve. See FIGS. 3–6.

By choice of the desired predetermined shape of the guiding introducer in conjunction with fluoroscopic viewing, the distal portion of the guiding introducer can be manipulated to direct the distal end of a catheter (5) placed within the lumen of the guiding introducer or sheath (4) to a specific internal surface within the right atrium. In addition, by providing sufficient rigidity, the distal end of the guiding catheter can be maintained in that fixed location or surface position of the endocardial structure to permit the appropriate procedures to be performed. If sensing procedures are involved, the guiding introducer is placed in the desired location. At that point, the electrical activity of the heart peculiar to that location can be precisely determined by use of an electrophysiology catheter (5) placed within the guiding introducer or sheath (4). Further, as the guiding introducer permits precise location of catheters, an ablation catheter may be placed at a precise location for destruction by the use of energy, for example, radio frequency, thermal, laser or direct current. This precise location of the ablation catheter tip is important as there will be no dilution of the energy delivered due to unfocused energy being dissipated over the entire cardiac chamber and lost in the circulating blood by a constantly moving tip of the ablating catheter. This permits a significantly reduced amount of energy to be applied, while still achieving efficient ablation. Further, time used to perform the procedure is significantly reduced over procedures where no guiding introducer is used.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A method for the mapping and ablation of anomalous conduction pathways within the right atrium of the heart comprising
    (a) introducing into the right atrium of the heart a precurved, guiding introducer, wherein said introducer contains a lumen passing therethrough, a proximal end and a distal end;
    (b) introducing into the lumen of the precurved, guiding introducer a catheter for mapping and ablation of anomalous conduction pathways within the right atrium of the heart, wherein said catheter has one or more electrodes located at or near a distal tip of the catheter; and
    (c) extending said distal tip of the catheter through the lumen of the guiding introducer and beyond the distal tip of the guiding introducer to allow the electrodes of the catheter to map and ablate one or more anomalous conduction pathways within the right atrium of the heart.

2. The method for mapping and ablation of claim 1 wherein the ablation procedure utilizes an energy source chosen from radio frequency, thermal, laser or direct current.

3. The method for the mapping and ablation of anomalous conduction pathways of claim 2 wherein the energy used for ablation is radio frequency energy.

4. The method for the mapping and ablation of anomalous conduction pathways of claim 1 wherein the guiding introducer is comprised of a first, second and third section wherein the first section is a generally elongated straight section, wherein merged with the distal end of said first section is the second section which is a curved section curved in a longitudinal curve with a radius of about 0.5 cm. to about 2.0 cm. to form an arc of approximately 40 to about 60 degrees, wherein merged with the distal end of the second section is the third section which is comprised of two portions, a generally straight portion directed at an angle of approximately 40 to about 60 degrees in relation to the first section, wherein said straight section is approximately 0.5 to about 3.0 cm. in length, and a longitudinally curved portion which is curved with an arc of about 35° to about 190°, and wherein both portions of the third section are substantially coplanar.

5. The method for the mapping and ablation of anomalous conduction pathways of claim 4 wherein the arc of the longitudinally curved portion of the third section is about 35 to about 55 degrees.

6. The method for the mapping and ablation of anomalous conduction pathways of claim 4 wherein the arc of the longitudinally curved portion of the third section is about 40 to about 50 degrees.

7. The method for the mapping and ablation of anomalous conduction pathways of claim 4 wherein the arc of the longitudinally curved portion of the third section is about 80 to about 100 degrees.

8. The method for the mapping and ablation of anomalous conduction pathways of claim 4 wherein the arc of the longitudinally curved portion of the third section is about 85 to about 95 degrees.

9. The method for the mapping and ablation of anomalous conduction pathways of claim 4 wherein the arc of the longitudinally curved portion of the third section is about 125 to about 145 degrees.

10. The method for the mapping and ablation of anomalous conduction pathways of claim 4 wherein the arc of the longitudinally curved portion of the third section is about 130 to about 140 degrees.

11. The method for the mapping and ablation of anomalous conduction pathways of claim 4 is wherein the arc of the longitudinally curved portion of the third section is about 170 to about 190 degrees.

12. The method for the mapping and ablation of anomalous conduction pathways of claim 4 wherein the arc of the longitudinally curved portion of the third section is about 175 to about 185 degrees.

13. A method for the treatment of Wolff-Parkinson-White syndrome within the right atrium of the heart comprising
    (a) introducing into the right atrium of the heart a precurved, guiding introducer, wherein said introducer contains a lumen passing therethrough, a proximal and a distal tip;
    (b) introducing into the lumen of the precurved, guiding introducer a catheter within the right side of the heart wherein said catheter has one or more electrodes located at or near a distal tip of the catheter;
    (c) extending said distal tip of the catheter through the lumen of the introducer and beyond the distal tip of the introducer to permit the electrodes of the catheter to ablate anomalous conduction pathways within the right side of the heart as a treatment for Wolff-Parkinson-White syndrome.

14. A method for the mapping and ablation of anomalous conduction pathways within the right atrium of the heart comprising
    (a) introducing into the right atrium of the heart a precurved, guiding introducer, wherein said introducer contains a lumen passing therethrough, a proximal end and a distal end, wherein the guiding introducer comprises a first, second and third sections, wherein the first section comprises a generally elongated straight section contained in a generally flat plane, wherein merged with the distal end of said first section of said introducer is the second section which comprises a curved section curved in a longitudinal curve from the first section with a radius of about 0.5 cm. to about 2.5 cm. to form an arc of approximately 40 to 60 degrees, and wherein merged with the distal end of the second section is the third section, wherein said third section is directed at an angle of approximately 40 to 60 degrees from the plane of the first section;

(b) introducing into the lumen of the precurved, guiding introducer a catheter for mapping and ablation of anomalous conduction pathways within the right atrium of the heart, wherein said catheter has one or more electrodes located at or near a distal tip of the catheter; and (c) extending said distal tip of the catheter through the lumen of the guiding introducer and beyond the distal tip of the guiding introducer to allow the electrodes of the catheter to map and ablate one or more anomalous conduction pathways within the right atrium of the heart.

15. The method for the mapping and ablation of anomalous conduction pathways of claim 14 wherein the generally straight portion of the third section is approximately 0.5 cm. to about 3.0 cm. in length.

16. A method for the mapping and ablation of anomalous conduction pathways within the right atrium of the heart comprising (a) introducing into the right atrium of the heart a precurved, guiding introducer, wherein said introducer contains a lumen passing therethrough, a proximal end and a distal end wherein the guiding introducer comprises a first, second and third section, wherein the first section is a generally elongated straight section, wherein merged with the distal end of said first section is the second section which comprises a curved section curved in a longitudinal curve with a radius of about 0.5 cm. to about 2.0 cm. to form an arc of approximately 40 to about 60 degrees, wherein merged with the distal end of the second section is the third section which comprises two portions, a generally straight portion directed at an angle of approximately 40 to about 60 degrees in relation to the first section, wherein said straight section is approximately 0.5 to about 3.0 cm. in length, and a longitudinally curved portion which is curved with an arc of about 35° to about 190°, and wherein both portions of the third section are substantially coplanar;

(b) introducing into the lumen of the precurved, guiding introducer a catheter for mapping and ablation of anomalous conduction pathways within the right atrium of the heart, wherein said catheter has one or more electrodes located at or near a distal tip of the catheter;

(c) extending said distal tip of the catheter through the lumen of the guiding introducer and beyond the distal tip of the guiding introducer to allow the electrodes of the catheter to map and ablate one or more anomalous conduction pathways within the right atrium of the heart.

17. A method for the treatment of Wolff-Parkinson-White syndrome within the right atrium of the heart comprising (a) introducing into the right atrium of the heart a precurved, guiding introducer, wherein said introducer contains a lumen passing therethrough, a proximal and a distal tip wherein the first section comprises a generally elongated straight section contained in a generally flat plane, wherein merged with the distal end of said first section of said introducer is the second section which comprises a curved section curved in a longitudinal curve from the first section with a radius of about 0.5 cm. to about 2.5 cm. to form an arc of approximately 40 to 60 degrees, and wherein merged with the distal end of the second section is the third section, wherein said third section is directed at an angle of approximately 40 to 60 degrees from the plane of the first section;

(b) introducing into the lumen of the precurved, guiding introducer a catheter within the right side of the heart wherein said catheter has one or more electrodes located at or near a distal tip of the catheter; and (c) extending said distal tip of the catheter through the lumen of the introducer and beyond the distal tip of the introducer to permit the electrodes of the catheter to ablate anomalous conduction pathways within the right side of the heart as a treatment for Wolff-Parkinson-White syndrome.

* * * * *